United States Patent [19]

Farina et al.

[11] Patent Number: 5,300,638
[45] Date of Patent: Apr. 5, 1994

[54] ASYMMETRIC SYNTHESIS OF TAXOL SIDE CHAIN

[75] Inventors: Vittorio Farina, West Hartford; Sheila I. Hauck, West Haven, both of Conn.

[73] Assignee: Bristol-Myers Squibb Company, New York, N.Y.

[21] Appl. No.: 914,909

[22] Filed: Jul. 16, 1992

Related U.S. Application Data

[63] Continuation of Ser. No. 739,018, Jul. 31, 1991, abandoned.

[51] Int. Cl.$^5$ .................... C07D 205/08; C07B 53/00
[52] U.S. Cl. ........................................ 540/357; 540/354
[58] Field of Search ................................ 540/354, 357

[56] References Cited

U.S. PATENT DOCUMENTS 4,924,011 5/1990 Denis et al. .................... 549/511
4,996,314 2/1991 Yoshioka ........................ 540/364

FOREIGN PATENT DOCUMENTS 400971 12/1990 European Pat. Off. .

OTHER PUBLICATIONS

Denis et al., *J. Org. Chem.*, 1990, 55:1957–1959.
Palomo et al., *Tet. Lett.*, 1990, 31:6429–6432.
Ojima et al., *J. Org. Chem.*, 1991, 56:1681–1683.
Bose et al., *J. Org. Chem.*, 1982, 47:4075–4081.
Tenneson and Belleau, *Can. J. Chem.*, 1980, 58:1605–1607.
Wagle et al., *J. Org. Chem.*, 1988, 53:4227–4236.
Wharton et al., *J. Chem. Soc. Perkin Trans. I*, 1984, 29–39.
Georg et al., *Tet. Lett.*, 1991, 32(27):3151–3154.
Furura, *Syn Lett*, p. 761 (1992).

*Primary Examiner*—Mark L. Berch
*Attorney, Agent, or Firm*—William T. Han

[57] ABSTRACT

The present invention relates to a process for the preparation of (3R, 4S)-3-hydroxy-4-phenyl-2-azetidinone derivatives which are useful intermediates in the synthesis of taxol from baccatin III, said process comprises reacting an acyloxyacetyl halide with an imine derived from L-threonine; and to compounds of formula (III) which are produced in said process:

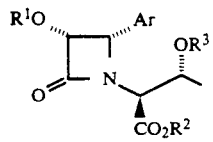

wherein Ar is phenyl; $R^1$ is hydrogen, an acyl radical of a carboxylic acid, or a carbonic acid ester radical; $R^2$ is hydrogen or a carboxy protecting group; and $R^3$ is hydrogen or a hydroxy protecting group.

6 Claims, No Drawings

ASYMMETRIC SYNTHESIS OF TAXOL SIDE CHAIN

CROSS-REFERENCE TO RELATED APPLICATION

This application is a continuation of our pending application Ser. No. 07/739,018 filed Jul. 31, 1991.

BACKGROUND OF THE INVENTION

1. Field of the Invention

The present invention relates to novel chiral intermediates for taxol side chain, and to a novel process for the preparation of these intermediates.

2. Background Art

Taxol (I) is a natural product that has been shown to display excellent antitumor activity both in vitro and in vivo, and recent studies have elucidated its unique mode of action, which involves abnormal polymerization of tubulin and disruption of mitosis. It is currently undergoing clinical trials in the United States and France and preliminary results have confirmed it as a most promising chemotherapeutic agent.

The clinical success of taxol has brought forth considerable concern over its supply. Taxol is extracted from the bark of slow-growing yew trees by difficult and low-yielding isolation process, and the need to harvest large number of yew trees has also raised ecological concerns. The observation that a related substance, 10-deacetyl baccatin III (II), is present in large amounts in the leaves of Taxus baccata has led several research teams to devise semisynthetic routes to taxol starting from 10-deacetyl baccatin III.

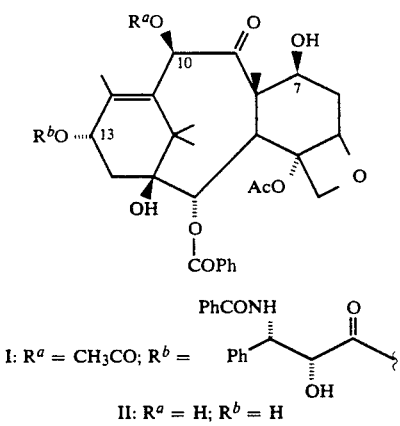

I: $R^a$ = CH$_3$CO; $R^b$ = Ph—CH(OH)—CH(NHCOPh)—C(O)—

II: $R^a$ = H; $R^b$ = H

Denis et al U.S. Pat. No. 4,924,011 discloses the preparation of taxol by reacting 7-triethylsilylbaccatin III and (2R, 3S)-N-benzoyl-O-(1-ethoxyethyl)-3-phenylisoserine followed by removal of the protecting groups. An improved synthesis of chiral 3-phenylisoserine compounds is reported in Denis et al, *J. Org. Chem.*, 1990, 55:1957–1959.

Holton in European Application 400,971 published Dec. 5, 1990 discloses the use of hydroxy protected 1-benzoyl-3-hydroxy-4-phenyl-2-azetidinone as the C-13 side chain of taxol in the acylation of protected baccatin III. The azetidinone is formed by the condensation of an acyloxyacetyl chloride and N-benzylidene-p-methoxy-aniline; however, the product so formed is a racemic mixture which requires resolution to obtain the desired enantiomer. The synthesis of the named azetidinone by the above-described method is also reported by Palomo et al in *Tet. Lett.*, 1990, 31:6529–6432.

Ojima et al in *J. Org. Chem.*, 1991, 56:1681–1683, report the condensation of (silyloxy)acetates bearing a chiral auxiliary with N-(trimethylsilyl)imines to give 3-hydroxy-4-aryl-2-azetidinones in high enantiomeric purity. However, the chiral (silyloxy)acetates are neither commercially available nor inexpensive to prepare requiring enzymatic resolution.

Chiral synthesis of 2-azetidinones is also of importance in other areas of medicinal chemistry, most notably in the β-lactam antibiotic area. Bose et al in *J. Org. Chem.*, 1982, 47:4075–4081 report the condensation of azidoacetyl chloride with a N-(phenylpropenylidene)-D-threonine ester to form the correspondingly substituted cis-2-azetidinone as a 1:1 diastereomeric mixture. Tenneson and Belleau in *Can. J. Chem.*, 1980, 58:1605–1607 report that when the hydroxy group of a N-(phenylpropenylidene)-D-threonine ester is protected with t-butyldimethylsilyl group, the product cis-2-azetidinone is obtained in 9:1 diastereomeric ratio. Wagle et al in *J. Org. Chem.*, 1988, 53:4227–4236 allude to a similar reaction in which triphenylsilyl is used as the hydroxy protecting group to give a 95:5 diastereomeric mixture.

Although the reported cyclocondensation reactions utilizing an imine derived from hydroxy protected D-threonine and azidoacetyl chloride result in high diastereoselectivity, such favorable outcome cannot be extrapolated to reactants bearing other substituents since this type of reaction is known to be sensitive to the type of substituents used in both reaction partners. For example, Wharton et al in *J. Chem. Soc. Perkin Trans. I*, 1984, 29–39 reports the cyclocondensation of N-benzylidene-L-Ala-L-Pro t-butyl ester with inter alia phenoxyacetyl chloride or benzyloxyacetyl chloride; however, the product yield was very low, and there was virtually no diastereoselectivity.

In our own experience, we found that reaction of benzyloxyacetyl chloride with N-benzylidene-o-(diphenyl-t-butylsilyl)-(L)-threonine p-nitrobenzyl ester resulted in a 2:1 diastereomeric mixture of the azetidinone; and when t-butyldiphenylsilyloxyacetyl chloride was used, no azetidinone was isolated. Thus it was unexpected that the use of an acyloxyacetyl chloride in the cyclocondensation would result in a better than 10:1 diastereomeric mixture of azetidinones favoring the desired diastereomer.

SUMMARY OF THE INVENTION

The present invention provides (3R,4S)-2-azetidinone derivatives having the formula (III)

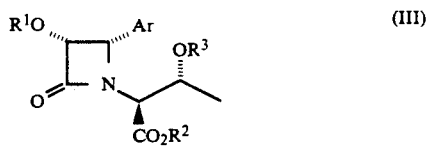

(III)

wherein Ar is phenyl; $R^1$ is hydrogen, an acyl radical of a carboxylic acid, or a carbonic acid ester radical; $R^2$ is hydrogen or a carboxy protecting group; and $R^3$ is hydrogen or a hydroxy protecting group.

Another aspect of the invention provides a process for the preparation of a compound of formula (IIIa)

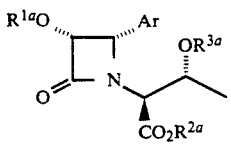 (IIIa)

which comprises the steps of (a) reacting an imine derivative of (L)-threonine of formula (IV)

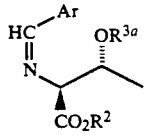 (IV)

wherein Ar is phenyl, $R^{2a}$ is a carboxy protecting group, and $R^{3a}$ is a hydroxy protecting group; with an acetyl halide of formula (V)

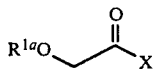 (V)

wherein $R^{1a}$ is an acyl radical of a carboxylic acid or a carbonic acid ester radical; and X is a halogen; in an inert organic solvent and in the presence of a base; and (b) separating the desired diastereomer. Preferably, the imine is generated in situ by reacting a hydroxy protected (L)-threonine with benzaldehyde.

Another aspect of the present invention provides a process for the preparation of an (3R,4S)-2-azetidinone derivative having the formula (VI)

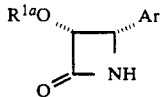 (VI)

wherein Ar is phenyl, and $R^{1a}$ is an acyl radical of a carboxylic acid or a carbonic acid ester radical; which comprises the steps of (a) reacting an imine derivative of (L)-threonine of formula (IV) with an acetyl halide of formula (V) in an inert organic solvent and in the presence of a base; (b) separating the desired diastereomer; and (c) removing the (L)-threonine chiral template. Preferably, the imine is generated in situ by reacting a hydroxy protected (L)-threonine with benzaldehyde.

The intermediates and processes of the present invention provide an economical and efficient route to key compounds, namely (3R,4S)-3-hydroxy-4-phenyl-2-azetidinone and its hydroxy protected congeners, in the synthesis of taxol or its derivatives from baccatin III.

DETAILED DESCRIPTION OF THE INVENTION

The present invention provides an (3R,4S)-2-azetidinone derivative having the formula (III)

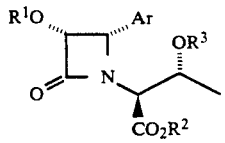 (III)

wherein Ar is phenyl; $R^1$ is hydrogen, an acyl radical of a carboxylic acid, or a carbonic acid ester radical; $R^2$ is hydrogen or a carboxy protecting group; and $R^3$ is hydrogen or a hydroxy protecting group. A compound of formula (III) may be further modified to provide the compound (3R,4S)-3-hydroxy-4-phenyl-2-azetidinone and its hydroxy protected congeners which are useful intermediates in the process of the synthesis of taxol and derivatives thereof from baccatin III.

As used herein, unless otherwise specified, "lower alkyl" represents straight or branched carbon chains having one to five carbon atoms. "Lower alkenyl" represents straight or branched carbon chains having at least one carbon-carbon double bond and having two to five carbon atoms. "Halogen" includes fluorine, chlorine, bromine and iodine. Since it is apparent from the definitions of $R^1$, $R^2$, $R^3$, $R^{1a}$, $R^{2a}$, and $R^{3a}$ that $R^1$ may also be defined as being hydrogen or $R^{1a}$, $R^2$ as hydrogen or $R^{2a}$, and $R^3$ as hydrogen or $R^{3a}$, this simpler terminology will be used throughout the specification.

"Acyl radical of a carboxylic acid" refers to an ester group $R^c$—CO— wherein $R^c$ may be (but is not limited to) hydrogen; lower alkyl such as methyl, ethyl, propyl, isopropyl and the like; halo-substituted lower alkyl such as chloromethyl, dichloromethyl, trichloromethyl, trifluoromethyl; substituted methyl such as methoxymethyl, triphenylmethoxymethyl, phenoxymethyl, p-chlorophenoxymethyl; phenyl and substituted phenyl such as 2,4,6-trimethylphenyl, o-methoxycarbonylphenyl; phenethyl and propenyl. "Carbonic acid ester radical" refers to carbonates $R^d$—O—CO— wherein $R^d$ may be (but is not limited to) lower alkyl such as methyl, ethyl, propyl, isobutyl; substituted ethyl such as 2,2,2-trihaloethyl, e.g. 2,2,2-trichloroethyl, 2-(trimethylsilyl)ethyl, 2-(phenylsulfonyl)ethyl; lower alkenyl such as vinyl and allyl; cinnamyl; p-nitrophenyl; benzyl and subsituted benzyl such as 3,4-dimethoxybenzyl, p-methoxybenzyl, o-nitrobenzyl and p-nitrobenzyl.

"Hydroxy protecting group" may be any that is conventionally used to block a hydroxy group. Examples of hydroxy protecting group include carbonates $R^c$—O—CO— wherein $R^c$ may be (but is not limited to) lower alkyl such as methyl, ethyl, propyl, isobutyl; substituted ethyl such as 2,2,2-trihaloethyl, e.g. 2,2,2-trichloroethyl, 2-(trimethylsilyl)ethyl, 2-(phenylsulfonyl)ethyl; lower alkenyl such as vinyl and allyl; cinnamyl; p-nitrophenyl; benzyl and substituted benzyl such as 3,4-dimethoxybenzyl, p-methoxybenzyl, o-nitrobenzyl and p-nitrobenzyl; esters $R^d$—CO— wherein $R^d$ may be (but is not limited to) hydrogen; lower alkyl such as methyl, ethyl, propyl, and the like; halo-substituted lower alkyl such as chloromethyl, dichloromethyl, trichloromethyl, trifluoromethyl; substituted methyl such as methoxymethyl, triphenylmethoxymethyl, phenoxymethyl, p-chlorophenoxymethyl; phenyl and substituted phenyl such as 2,4,6-trimethylphenyl, o-methoxycarbonylphenyl; phenethyl and propenyl; and ethers $R^e$ wherein $R^e$ may be (but is not limited to) methoxymethyl, tetrahydropyranyl, tetrahydrofuranyl, benzyloxymethyl, t-butoxymethyl, 2-methoxyethoxymethyl, 2,2,2-trichloroethoxymethyl, ethoxyethyl, 2,2,2-trichloroethyl, t-butyl, allyl, p-chloroph benzyl, p-methoxy-benzyl, o-nitrobenzyl, p-nitrobenzyl, p-chlorobenzyl, p-cyanobenzyl, diphenylmethyl, triphenylmethyl, or a triorganosilyl group, for example, trimethylsilyl, triethylsilyl, isopropyldimethylsily, t-butyldimethylsilyl, (triphenylmethyl)dimethylsily, t-butyldiphenylsilyl, methyldiisopropylsilyl, t-butoxydiphenylsilyl and triphenylsilyl.

"Carboxy protecting group" includes (but is not limited to) lower alkyl such as methyl, ethyl, propyl, and t-butyl; substituted lower alkyl such as 9-fluorenylmethyl, methoxymethyl, methoxyethoxymethyl, benzyloxymethyl, phenacyl, p-bromophenacyl, α-methylphenacyl, 2,2,2-trichloroethyl, 2-haloethyl, 2-(trimethylsilyl)ethyl; allyl; phenyl; benzyl; substituted benzyl such as triphenylmethyl, diphenylmethyl, 2,4,6-trimethylbenzyl, p-bromobenzyl, o-nitrobenzyl, p-nitrobenzyl, p-methoxybenzyl, and 2,6-dimethoxybenzyl; and triorganosilyl such as trimethylsilyl, triethylsilyl, t-butyldimethylsilyl, isopropyldimethylsilyl, phenyldimethylsilyl and di-t-butylmethylsilyl.

Additional examples of protecting groups as well as methods for introducing and removing protecting groups may be found in standard textbooks such as Green and Wutz, *Protective Groups in Organic Synthesis*, 2d Edition, John Wiley & Sons, Inc., 1991.

In one preferred embodiment, $R^1$ is an acyl radical of a carboxylic acid, preferably a lower alkanoyl group; and most preferably $R^1$ is the acetyl group. In another preferred embodiment, $R^3$ is a bulky triorganosilyl group, preferably t-butyldimethylsilyl, t-butyldiphenylsilyl or t-butoxydiphenylsilyl; and most preferably $R^3$ is the t-butyldiphenylsilyl or t-butoxydiphenylsilyl group. In another preferred embodiment, $R^2$ is selected from methyl, ethyl, allyl, and p-nitrobenzyl; and most preferably $R^2$ is p-nitrobenzyl or methyl. Particularly preferred embodiments are compounds of formula (III) wherein $R^1$ is acetyl, $R^2$ is methyl or p-nitrobenzyl, and $R^3$ is t-butyldiphenylsilyl or t-butoxydiphenylsilyl.

Compounds of formula (III) in which $R^1$ is $R^{1a}$, $R^2$ is $R^{2a}$, and $R^3$ is $R^{3a}$ (IIIa) are prepared by reacting a hydroxy and carboxy protected N-benzylidene-(L)-threonine of formula (IV) with an acetyl halide of formula (V) as illustrated in Scheme I.

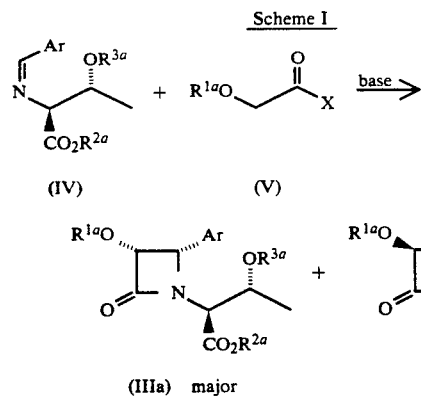

In Scheme I, Ar; $R^{1a}$, $R^{2a}$ and $R^{3a}$ are as previously defined; and X is a halogen such as chlorine, bromine and iodine. The cyclocondensation reaction is carried out in an inert organic solvent such as methylene chloride, chloroform, tetrahydrofuran and the like, and in the presence of a base, preferably a tertiary amine base such as triethylamine, trimethylamine, diisopropylethylamine, and the like; and at temperature below 0° C., e.g. at about −5° to about −40° C. The resulting product is a diastereomeric mixture in a ratio of at least 10:1 favoring the desired (3R,4S)-azetidinone (IIIa). The diastereomeric mixture may be separated by conventional methods such as recrystallization or chromatography; but more advantageously, on a large scale the desired diastereomers may be separated by simple recrystallization. The separation of the diastereomers may be effected either right after the formation of the azetidine ring or after the removal of one or more of the protecting groups.

The starting materials for the above reaction may be prepared from readily available reagents. Thus, imines of formula (IV) are prepared from (L)-threonine and benzaldehyde according to known methods; and compounds of formula (V) are prepared from glycolic acid with an appropriate acylating agent.

In a preferred process, the imine is generated in situ by reacting a hydroxy and carboxy protected (L)-threonine with benzaldehyde in an inert organic solvent such as methylene chloride, chloroform, tetrahydrofuran and the like. The reaction is preferably carried out in the presence of a water scavenger, such as molecular sieves and at a temperature conducive to imine formation, e.g. at ambient temperature. The product thus formed, i.e. a compound of formula (IV), is used, without isolation, in the cyclocondensation reaction described above.

Compounds of formula (IIIa) may be converted to compounds of formula (III) in which at least one of $R^1$, $R^2$ or $R^3$ is hydrogen. Thus at least one of $R^{1a}$, $R^{2a}$ or $R^{3a}$ of a compound of formula (IIIa) is replaced with hydrogen using conventional deprotecting methods, and the choice of the method used will depend on the identity of the protecting group. Given the protecting group the selection of a suitable deprotecting procedure is within the ability of a person skilled in the art. For example, base hydrolysis may be used to remove the carboxy protecting group $R^{2a}$, and to remove $R^{1a}$ where it is an alkanoyl group; where $R^{1a}$ is 2,2,2-trichlorethoxycarbonyl, it can be removed by e.g. zinc/acetic acid; where $R^3$ is t-butyldiphenylsilyl, it can be removed with hydrogen fluoride/pyridine, and where $R^3$ is t-butoxydiphenylsilyl, it can be removed with tetrabutylammonium fluoride/acetic acid. Further examples may be found in Green and Wutz, Protective Groups in Organic Synthesis, 2d Edition, John Wiley & Sons, Inc., 1991.

The (L)-threonine chiral template on a compound of formula (IIIa) may be removed by a three step process as illustrated in Scheme II.

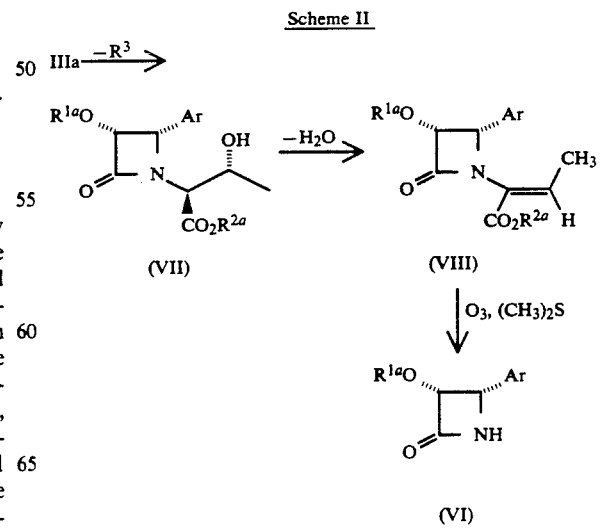

First, the hydroxy protecting group $R^3$ is removed. As previously described, deprotection may be effected by different methods depending on the protecting group chosen. As an example, the t-butyldiphenylsilyl protecting group may be removed by hydrogen fluoride/pyridine, and the t-butoxydiphenylsilyl protecting group may be removed with tetrabutylammonium fluoride/acetic acid.

The second step involves dehydration of the alcohol (VII) to give the corresponding acrylate derivative (VIII). Dehydration may be accomplished by a variety of methods, for example by treatment with iodine, phosphorous pentoxide, thionyl chloride, thionyl bromide, or $Ph_3P(OSO_2CF_3)_2$. A convenient method is to convert the hydroxy group to a sulfonate, e.g. by reacting it with toluenesulfonyl chloride, toluenesulfonic anhydride, methanesulfonyl anhydride or methanesulfonyl chloride at low temperature, e.g. at $-78°$ C,; in the presence of a base such as triethylamine; maintaining the reaction mixture at e.g. room temperature for several hours effects elimination of the sulfonate to give the olefin (VIII).

The third step involves ozonolysis of the olefin (VIII) to provide the azetidinone (VI). Ozonolysis is carried out in an organic solvent e.g. in a mixture of methylene chloride and methanol, at a low temperature, e.g. at about $-78°$ C. The ozonide thus formed is decomposed with a reagent suitable for such purpose; examples of suitable reagent include zinc/acetic acid, catalytic hydrogenation, trimethyl phosphite, thiourea, triphenylphosphine and dimethyl sulfide. Preferably, dimethyl sulfide is used. The reaction solution is allowed to warm to room temperature yielding the desired azetidinone (VI). It has been noted that where $R^{2a}$ is methyl, it is preferred that following the decomposition of the ozonide and warming, the resulting solid material be dissolved in an inert organic solvent such as tetrahydrofuran and treated with hydrazine hydrate at $-78°$ C. to yield the azetidinone (VI).

A compound of formula (VI) may be converted to the compound (3R,4S)-3-hydroxy-4-phenyl-2-azetidinone (IX) by removing the $R^{1a}$ group. The deblocking can be accomplished by methods well known in the art; for example, where $R^1$ is acetyl, it can be removed by base hydrolysis. Compound (IX) may be further elaborated to provide a hydroxy protected (3R,4S)-1-benzoyl-3-hydroxy-4-phenyl-2-azetidinone which can then be used to acylate baccatin III to give taxol. For example, according to the methods disclosed in European Patent Application No. 400, 971, compound (IX) is treated with ethyl vinyl ether and a catalytic amount of methanesulfonic acid to give (3R,4S)-3-(1-ethoxyethoxy)-4-phenyl-2-azetidinone. The latter is then treated with n-butyllithium followed by benzoyl chloride to give the product (3R,4S)-1-benzoyl-3-(1-ethoxyethoxy)-4-phenyl-2-azetidinone. This product is then reacted with 7-O-triethylsilyl baccatin III in pyridine and in the presence of dimethylaminopyridine to give taxol following the removal of the triethylsilyl protecting group.

Alternatively, compound (IX) can be converted to (2R,3S)-N-benzoylphenylisoserine as described in Ojima et al, *J. Org. Chem.*, 1991, 56:1681-1683; a suitably hydroxy-protected (2R,3S)-N-benzoylphenylisoserine is then used to acylate 7-O-triethylsilyl baccatin III according to the procedure described in U.S. Pat. No. 4,924,011.

The following examples are offered to more fully illustrate the invention disclosed and claimed herein; they shall not be construed in any manner to limit the scope of the invention which is defined solely by the claims appended hereto.

EXAMPLE 1

Preparation of p-nitrobenzyl 3-acetoxy-α-[[(1-t-butyldiphenylsilyl)oxy]ethyl]-2-oxo-4-phenyl-1-azetidineacetate. (compound 1)

(a) o-t-butyldiphenylsilyl-(L)-threonine p-nitrobenzyl ester (compound 2)

(L)-Threonine p-nitrobenzyl ester tosylate (10.0 g, 0.0234 mol) (prepared according to the procedure reported in Bose, A.K. et al, *J. Org. Chem.*, 1982, 47:4075-4081) in anhydrous $CH_2Cl_2$(100 mL) was stirred in the presence of imidazole (3.130 g, 0.0468 mol) and diphenyl-t-butylsilyl chloride (6.70 mL, 0.0257 mol) for 16 h at room temperature. The solids were removed by filtration. Partition of the product between $CH_2Cl_2$ and water, followed by washing the organics with 5% aqueous bicarbonate and water, drying and evaporation, gave a crude oil. Flash chromatography (65% ethyl acetate in hexane) gave compound 2 as an oil (9.60 g, 83%).

NMR (CDCl$_3$) δ 8.13 (d, J=8.7 Hz, 2H) 7.58-7.24 (m, 12H) 5.15 (d, J=13.3 Hz, 1H) 4.93 (d, J=13.3 Hz, 1H) 4.34 (m, 1H) 3.34 (d, J=2.5 Hz, 1H) 1.12 (d, J=6.4 Hz, 3H) 0.98 (s, 9H). HRMS, calcd. for $C_{27}H_{33}N_2O_5Si$: 493.2159, found 493.2150.

(b) preparation of compound 1

Compound 2 (1.473 g, 2.980 mmol) was stirred with benzaldehyde (0.60 ml, 5.97 mmol) in anhydrous $CH_2Cl_2$ (10 mL) in the presence of molecular sieves at room temperature for 16 h. The solution was cooled to $-30°$ C. and triethylamine (0.789 mL, 5.662 mmol) was added, followed by acetoxyacetyl chloride (0.609 mL, 5.662 mmol) as a $CH_2Cl_2$ solution (5 mL) over 20 min. The mixture was allowed to reach room temperature overnight and worked up by partitioning between $CH_2Cl_2$ and water. The organics were further washed with 0.1N HCl, 5% bicarbonate and brine, then dried over magnesium sulfate. Flash chromatography yielded a diastereomeric mixture of compound 1 (1.710 g, 84%) [(3R, 4S):(3S, 4R)=91:9 as determined by NMR].

NMR (CDCl$_3$) δ 8.22-8.19 (m, 2H) 7.60-7.08 (m, 17H) 5.93 (d, J=5.2 Hz, 1H major product) 5.79 (d, J=5.0 Hz, 1H minor product) 5.43 (d, J=5.2 Hz, 1H major) 5.27 (d, J=13.2 Hz, 1H major) 5.04 (d, J=5 Hz, 1H minor) 4.98 (d, J=13.2 Hz, 1H major) 4.84 (d, J=13.2 Hz, 1H minor) 4.57 (d, J=13.2 Hz, 1H minor) 4.45 (m, 1H) 4.30 (m, 1H) 1.64 (s, 3H) 1.15 (d, J=6.2 Hz, 3H minor) 0.99 (d, J=6.2 Hz, 3H major) 0.88 (s, 9H). HRMS: Calcd for $C_{38}H_{41}N_2O_8Si$ (M+H) 681.2632, found 681.2639.

EXAMPLE 2

Preparation of methyl 3-acetoxy-α-[[(t-butyldiphenylsilyl)oxy]ethyl]-2-oxo-4-phenyl-1-azetidineacetate. (compound 3)

(a) O-t-butyldiphenylsilyl-(L)-threonine methyl ester. (compound 4)

(L)-Threonine methyl ester hydrochloride (Sigma Chemical Co., 1.190 g, 7.020 mmol) in anhydrous $CH_2Cl_2$ (10 mL) was stirred with imidazole (955 mg, 14.03 mmol) and diphenyl-t-butylsilyl chloride (2.0 mL, 7.720 mmol) for 16 h at room temperature. Work up and chromatography as in Example 1 (a) gave compound 4 (1.740 g, 67%) as a thick oil.

NMR (CDCl$_3$ δ 7.65–7.33 (m, 10H) 4.32 (m, 1H) 3.59 (s, 3H) 3.25 (d, J=2.5 Hz, 1H) 1.09 (d, J=6.2 Hz, 3H) 0.99 (s, 9H).

(b) preparation of compound 3

Compound 4 (472 mg, 1.270 mmol) in CH$_2$Cl$_2$ (5 mL) was treated with benzaldehyde (0.235 mL, 2.310 mmol) at room temperature overnight in the presence of molecular sieves. Upon cooling to −30° C., triethylamine (0.336 mL, 2.40 mmol) was added, followed by acetoxyacetyl chloride (0.258 mL, 2.40 mmol) over 10 min. The mixture was allowed to reach room temperature over 6 h. Work up and chromatography as in Example 1 (b) gave a diastereomeric mixture of compound 3 (464 mg, 65%). [(3R, 4S): (3S, 4R)=95:5 as determined by NMR].

NMR (CDCl$_3$) δ 7.60–7.01 (m, 15H) 5.97 (d, J=5 Hz, 1H major) 5.81 (d, J=5 Hz, 1H minor) 5.45 (d, J=5 Hz, 1H major) 5.04 (d, J=5 Hz, 1H minor) 4.40 (d, J=3 Hz, 1H) 4.27 (m, 1H) 3.69 (s, 3H major) 3.22 (s, 3H minor) 0.94 (d, J=6.2 Hz, 3H) 0.88 (s, 9H). HRMS, calcd. for C$_{32}$H$_{38}$NO$_6$Si: 560.2468, found 560.2487.

EXAMPLE 3

Preparation of compound 3 without isolation of intermediate (L)-Threonine methyl ester hydrochloride (20.73 g, 0.122 mol) was stirred in dry CH$_2$Cl$_2$ (200 mL) in the presence of imidazole (16.61 g, 0.244 mol), diphenyl-t-butylsilyl chloride (35.0 mL, 0.134 mol) and 4-dimethylaminopyridine (5–10 mg) for 16 h. The solids were filtered and the filtrate was washed with 5% aqueous bicarbonate and water, then dried over magnesium sulfate. After filtration, the solution was treated with benzaldehyde (25.0 mL, 0.244 mol) in the presence of molecular sieves (ca. 10 mL) for 18 h at room temperature. Upon cooling to −40° C., the solution was treated with triethylamine (32 mL, 0.232 mol), followed by a solution of acetoxyacetyl chloride (25 mL, 0.232 mol) in CH$_2$Cl$_2$ (25 mL) over 40 min. The solution was allowed to reach 0° C. over 5 h. Work up as in Example 2 (b) gave a crude oil, which was triturated with ether to give pure (3R, 4S) compound 3 (19.13 g, 28% yield over 3 steps), with no traces of the (3S, 4R) diastereomer. A second crop, of lower purity, can be obtained from the mother liquor.

EXAMPLE 4

Preparation of methyl 3-acetoxy-α-[[(t-butoxydiphenylsilyl)oxy]ethyl]-2-oxo-4-phenyl-1-azetidineacetate. (compound 5)

(a) O-t-butoxydiphenylsilyl-(L)-threonine methyl ester. (compound 6)

(L)-Threonine methyl ester hydrochloride (1.2625 g, 7.444 mmol) in anhydrous CH$_2$Cl$_2$ (15 mL) was stirred with imidazole (1.010 g, 14.89 mmol) and t-butoxydiphenylsilyl chloride (2.274 g, 7.816 mmol) for 16 h at room temperature. Work up as in Example 1 (a) gave compound 6 (2.881 g, 99%) as a thick oil. This was used as such in the next step.

NMR (CDCl$_3$) δ 7.70–7.25 (m, 10H) 4.44 (m, 1H) 3.62 (s, 3H) 3.31 (d, J=3 Hz, 1H) 2.12 (br, s 2H) 1.3–1.15 (m, 12H).

(b) preparation of compound 5

Compound 6 (548 mg, 1.414 mmol) in CH$_2$Cl$_2$ (10 mL) was treated with benzaldehyde (0.158 mL, 1.55 mmol) at room temperature overnight in the presence of molecular sieves. Upon cooling to −40° C., triethylamine (0.20 mL, 1.698 mmol) was added, followed by acetoxyacetyl chloride (0.182 mL, 1.698 mmol) over 10 min. The mixture was allowed to reach room temperature over 4 h. Work up and chromatography as in Example 1 (b) gave a diastereomeric mixture of compound 5 [(3R,4S):(3S,4R)=93:7 by as determined by (NMR)].

NMR (CDCl$_3$) δ 7.42–7.20 (m, 15H) 5.90 (d, J=5.1 Hz, 1H major) 5.68 (d, J=5 Hz, 1H minor) 5.39 (d, J=5.1 Hz, 1H major) 4.96 (d, J=5 Hz, 1H minor) 4.58 (m, 1H) 4.40 (br d, 1H) 3.68 (s, 3H major) 3.25 (s, 3H minor) 1.14 (s, 9H) 1.07 (d, J=6.6 Hz, 3H).

EXAMPLE 5

Preparation of p-nitrobenzyl (3R,4S)3-acetoxy-α-[(1-hydroxy)ethyl]-2-oxo-4-phenyl-1-azetidineacetate (compound 7) from compound 1.

The diastereomeric mixture of Example 1 (155.6 mg, 0.228 mmol) in anhydrous THF (1 mL) was stirred with HF/pyridine (4.4M, 0.52 mL, 2.28 mmol HF) at room temperature for 3 days. The solution was diluted with ethyl acetate and quenched into 5% sodium bicarbonate. The organic layer was washed with more bicarbonate, water, and brine. Drying and evaporation gave a crude product, which was chromatographed on silica with 30% ethyl acetate/hexane to give the title compound (75.7 mg).

NMR (CDCl$_3$) δ 8.19 (d, J=8.4 Hz, 2H) 7.67–7.24 (m, 7H) 5.89 (d, J=4.8 Hz, 1H) 5.22 (s, 2H) 5.07 (d, J=4.8 Hz, 1H) 4.36 (m, 1H) 4.01 (d, J=4.2 Hz, 1H) 3.05 (d, J=9.3 Hz, 1H) 1.72 (s, 3H) 1.23 (d, J=6.5 Hz, 3H). HRMS, calcd. for C$_{22}$H$_{23}$N$_2$O$_8$: 443.1454, found 443.1470.

EXAMPLE 6

Preparation of methyl (3R, 4S)-3-acetoxy-α-[(1-hydroxy)ethyl]-2-oxo-4-phenyl-1-azetidineacetate (compound 8) from compound 3.

The diastereomeric mixture of Example 2 (444 mg, 0.793 mmol) in anhydrous THF (4 mL) was treated with HF/pyridine (4.4M, 1.80 mL, 7.93 mmol) at room temperature for 5 days. Quench and work up as in the above Example 5, followed by chromatography (40% ethyl acetate/hexane) gave title compound as a white solid. (139 mg, 54%).

NMR (CDCl$_3$) δ 7.42–7.25 (m, 5H) 5.90 (d, J=4.8 Hz, 1H) 5.09 (d, J=4.8 Hz, 1H) 4.28 (m, 1H) 4.01 (d, J=4.8 Hz, 1H) 3.70 (s, 3H) 1.73 (s, 3H) 1.19 (d, J=6.6 Hz, 3H).

EXAMPLE 7

Preparation of compound 8 from compound 5

The diastereomeric mixture of Example 4 (245.1 mg, 0.414 mmol) in anhydrous THF (2 mL) were treated with acetic acid (0.15 mL) followed by tetrabutylammonium fluoride (1M in THF, 1.20 mL, 3 equiv). The solution was stirred for 14 h at room temperature, then partitioned between 5% aqueous sodium bicarbonate and ethyl acetate. Chromatography as in Example 6 gave compound 8 (66 mg, 50%). The NMR spectrum matches the one reported in Example 6.

EXAMPLE 8

Preparation of (3R,4S)-3-acetoxy-4-phenyl-2-azetidinone. (compound 9)

(a) p-nitrobenzyl (3R,4S)-3-acetoxy-α-ethylidene-4-phenyl-2-oxo-1-azetidineacetate (compound 10)

Compound 7 (75 mg, 0.169 mmol) was dissolved in CH$_2$Cl$_2$ at −78° C., and mesyl chloride (0.013 mL, 0.170 mmol) was added, followed by triethylamine (0.047 mL, 0.338 mmol). The reaction mixture was allowed to reach 0° C. and monitored for disappearance of starting material (TLC). Two more portions of mesyl chloride and triethylamine were added as above, and the mixture was stirred at room temperature for 4 h. Partition between water and ethyl acetate, followed by washing the organics with dilute bicarbonate, dilute HCl and brine, and drying gave a crude product, which was purified by flash chromatography (28%) ethyl acetate/hexane) to yield compound 10 (62.9 mg, 88%) as an oil.

NMR (CDCl$_3$) δ 8.19 (d, J=8.6 Hz, 2H) 7.44 (d, J=8.6 Hz, 2H) 7.34-7.21 (m, 5H) 6.95 (q, J=7.3 Hz, 1H) 5.92 (d, J=4.2 Hz, 1H) 5.64 (d, J=4.2 Hz, 1H) 5.28 (d, J=13.3 Hz, 1H) 5.18 (d, J=13.3 Hz, 1H) 2.08 (d, J=7.3 Hz, 3H) 1.71 (s, 3H). HRMS, calcd. for C$_{22}$H$_{21}$N$_2$O$_7$ (M+H): 425.1349, found 425.1363.

(b) preparation of compound 9

Compound 10 (41 mg, 0.0966 mmol) in CH$_2$Cl$_2$/MeOH (3 mL each) was treated at −78° C. with a stream of ozone until a blue color persisted. The solution was purged with nitrogen, and the ozonide decomposed with methyl sulfide (0.5 mL). The solution was allowed to reach room temperature, and stirred for 48 h. The product was isolated by evaporation and chromatography (30% ethyl acetate/hexane) to yield compound 9 (20 mg, 100%) as a white solid.

NMR (CDCl$_3$) δ 7.38-7.24 (m, 5H) 6.31 (br s, 1H) 5.87 (br m, 1H) 5.04 (d, J=4.8 Hz, 1H) 1.67 (s, 3H).

EXAMPLE 9

Preparation of compound 9 from compound 8

The procedure described in Example 8(a) was repeated using compound 8 instead of compound 7 to give methyl (3R,4S)-3-acetoxy-α-ethylidene-4-phenyl-2-oxo-1-azetidineacetate (compound 11).

The resulting crude compound 11 (6.2 g) was dissolved in dichloromethane and ozonized at −78° C. Quenching with methyl sulfide (5 mL) followed by warming to room temp. and evaporation gave a white solid. This was dissolved in THF (150 mL) and cooled to −78° C. Hydrazine hydrate (a total of 2.4 mL) was added in two equal portions, and the mixture was worked up after 2 h at −78° C. After partitioning between ethyl acetate and water and drying, the crude product was chromatographed (40% ethyl acetate/hexane) to afford compound 9 (2.13 g, 54% overall) as a colorless solid.

What is claimed is:

1. A process for the preparation of an (3R,4S)-2-azetidinone derivative having the formula

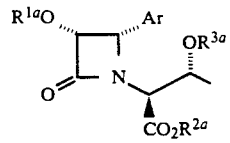

wherein
Ar is phenyl;
R$^{1a}$ is an acyl radical of a carboxylic acid or a carbonic acid ester radical;
R$^{2a}$ is a carboxy protecting group; and
R$^{3a}$ is a hydroxy protecting group selected from the group consisting of t-butyldiphenylsilyl and t-butoxydiphenylsilyl; which comprises the steps of
(a) reacting an imine derivative of (L)-threonine having the formula

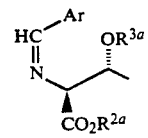

wherein Ar, R$^{2a}$ and R$^{3a}$ are as defined above; with an acetyl halide having the formula

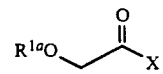

wherein R$^{1a}$ is as defined above and X is a halogen; in an inert organic solvent and in the presence of a base, to provide a diastereomeric product mixture in which the ratio of (3R,4S) to (4S,3R) of the azetinone derivative is at least 10:1; and (b) separating the desired diastereomer.

2. A process for the preparation of an (3R,4S)-2-azetidinone derivative having the formula

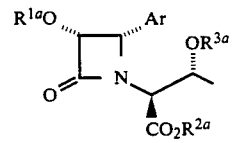

wherein
Ar is phenyl;
R$^{1a}$ is an acyl radical of a carboxylic acid or a carbonic acid ester radical;
R$^{2a}$ is a carboxy protecting group; and
R$^{3a}$ is a hydroxy protecting group selected from the group consisting of t-butyldiphenylsilyl and t-butoxydiphenylsilyl; which comprises the steps of
(a) reacting a (L)-threonine derivative having the formula

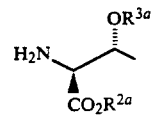

with an aldehyde ArC(O)H, wherein Ar, R$^{2a}$ and R$^{3a}$ are as defined above; (b) treating the resulting imine of step (a) with an acetyl halide having the formula

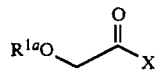

wherein $R^{1a}$ is as defined above and X is a halogen; in an inert organic solvent and in the presence of a base, to provide a diastereomeric product mixture in which the ratio of (3R,4S) to (4S,3R) of the azetinone derivative is at least 10:1; and (c) separating the desired diastereomer.

3. A process for the preparation of an (3R,4S)-2-azetidinone derivative having the formula

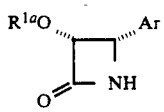

wherein $R^{1a}$ is is an acyl radical of a carboxylic acid or a carbonic acid ester radical; and Ar is phenyl; which comprises the steps of (a) reacting an imine derivative of (L)-threonine having the formula

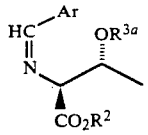 (IV)

wherein Ar, is as defined above; $R^{2a}$ is a carboxy protecting group; $R^{3a}$ is a hydroxy protecting group selected from the group consisting of t-butyldiphenylsilyl and t-butoxydiphenylsilyl; with an acyl halide having the formula

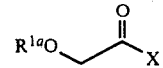

wherein $R^{1a}$ is as defined above and X is a halogen; in an inert organic solvent and in the presence of a base, to provide a diastereomeric product mixture in which the ratio of (3R,4S) to (4S,3R) of the azetidinone derivative is at least 10:1; (b) separating the desired diastereomer; and (c) removing the (L)-threonine group.

4. A process for the preparation of an (3R,4S)-2-azetidinone derivative having the formula

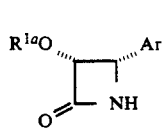

wherein $R^{1a}$ is an acyl radical of a carboxylic acid or a carbonic acid ester radical; and Ar is phenyl; which comprises the steps of (a) reacting a (L)-threonine derivative having the formula

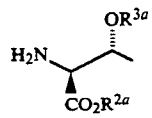

with an aldehyde ArC(O)H, wherein Ar, is as defined above; $R^{2a}$ is a carboxy protecting group; $R^{3a}$ is a hydroxy protecting group selected from the group consisting of t-butyldiphenylsilyl and t-butoxydiphenylsilyl; (b) treating the resulting imine of step (a) with an acyl halide having the formula

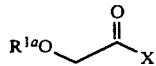

wherein $R^{1a}$ is as defined above and X is a halogen; in an inert organic solvent and in the presence of a base, to provide a diastereomeric product mixture in which the ratio of (3R,4S) to (4S,3R) of the azetidinone derivative is at least 10:1; (c) separating the desired diastereomer; and (d) removing the (L)-threonine group.

5. A process according to claim 3 wherein said removal of the (L)-threonine group comprises the steps of (a) removing the hydroxy protecting group $R^{3a}$; (b) eliminating the α-hydrogen atom and the hydroxy group to form an acrylate; and (c) treating the product of step (b) with ozone, and treating the resulting ozonide with a decomposing reagent.

6. A process according to claim 4 wherein said removal of the (L)-threonine group comprises the steps of (a) removing the hydroxy protecting group $R^{3a}$; (b) eliminating the α-hydrogen atom and the hydroxy group to form an acrylate; and (c) treating the product of step (b) with ozone, and treating the resulting ozonide with a decomposing reagent.

* * * * *